United States Patent [19]
Tankovich

[11] Patent Number: 6,083,217
[45] Date of Patent: *Jul. 4, 2000

[54] DESTRUCTION FOR UNWANTED TISSUE BY DEEP LASER HEATING OF WATER

[75] Inventor: Nikolai Tankovich, San Diego, Calif.

[73] Assignee: Lumedics, Ltd., San Diego, Calif.

[ * ] Notice: This patent is subject to a terminal disclaimer.

[21] Appl. No.: 08/949,387

[22] Filed: Oct. 14, 1997

Related U.S. Application Data

[63] Continuation of application No. 08/564,658, Nov. 29, 1995, abandoned.

[51] Int. Cl.$^7$ .................................................. A61K 5/06
[52] U.S. Cl. ..................................... 606/9; 606/3; 606/13
[58] Field of Search ....................... 606/3, 9–19; 128/898

[56] References Cited

U.S. PATENT DOCUMENTS

| | | |
|---|---|---|
| 3,660,777 | 5/1972 | Erickson . |
| 3,865,114 | 2/1975 | Sharon . |
| 4,564,012 | 1/1986 | Shimada et al. . |
| 4,566,453 | 1/1986 | Kumano et al. . |
| 4,583,526 | 4/1986 | Ali . |
| 4,733,660 | 3/1988 | Itzkan ........................................ 606/9 |
| 4,976,709 | 12/1990 | Sand . |
| 5,037,421 | 8/1991 | Boutacoff et al. . |
| 5,059,192 | 10/1991 | Zaias . |
| 5,207,671 | 5/1993 | Franken et al. . |
| 5,217,455 | 6/1993 | Tan . |
| 5,290,273 | 3/1994 | Tan . |
| 5,342,352 | 8/1994 | Franken et al. . |
| 5,344,418 | 9/1994 | Ghaffari . |
| 5,348,551 | 9/1994 | Spears et al. .............................. 606/5 |
| 5,348,552 | 9/1994 | Nakajima et al. . |

FOREIGN PATENT DOCUMENTS

| | | | |
|---|---|---|---|
| 1102613 | 7/1984 | U.S.S.R. ..................................... 606/2 |

OTHER PUBLICATIONS

Inci F. Cilesiz, et al., "Light dosimetry: effects of dehydration and thermal damage on the optical properties of the human aorta" Applied Optics vol. 32(4), 1993, pp. 477–487.
Kathy Kincade, "Wrinkles shrivel under file from pulsed lasers.", New Scientist, Jul. 1995, p. 25.
"Spectrum corners piece of the skin–resufacing market.", Biophotonics International, Jul./Aug. 1995, p. 32.
"Cosmetic lasers: in pursuit of lost youth.", Biophotonics International, Jul./Aug. 1995, pp. 61–62.
J. S. Nelson et al., "Dynamic epidermal cooling duuring pulsed laser treatment of port–wine stain. A new methodology with preliminary clinical evaluation.", Archives of Dermatology, Jun. 1995, 131(6):695–700.
B. Anvari et al., "Selective cooling of biological tissues: application for thermally mediated therapeutic procedures.", Physics in Medicine and Biology, Feb. 1995, 40(2):241–52.
S. Kimel et al., "Differential vascular response to laser photothermolysis.", Journal of Investigative Dermatology, Nov. 1994, 103(5):693–700.
"Selective Photothermolysis: Precise Microsurgery by Selective Absorption of Pulsed Radiation" by Anderson et al; Science; vol. 220, Apr. 29, 1983, pp. 524–527.

*Primary Examiner*—David M. Shay
*Attorney, Agent, or Firm*—Dan Hubert & Assoc.

[57] ABSTRACT

A process for destroying relatively deep formations of unwanted sub-epidermal tissue by heating water in the formations with a laser to denature proteins therein. In an exemplary embodiment, a laser beam is operated to irradiate a target region of highly vascularized dermal tissue in a blood-circulating living being, such as a human. The laser light preferably has a wavelength of about 1.45–1.68 $\mu$m. This operating parameter provides the laser beam with a low enough water absorption coefficient to facilitate adequate penetration in to the target area while still providing enough energy to heat water to a temperature capable of spatially conforming vascularized tissue in the target area.

27 Claims, 3 Drawing Sheets

DESTRUCTION FOR UNWANTED TISSUE BY DEEP LASER HEATING OF WATER

This application is a file wrapper continuation of application Ser. No. 08/564,658, filed Nov. 29, 1995, now abandoned.

BACKGROUND OF THE INVENTION

1. Field of the Invention

The present invention relates to the use of lasers to remove unwanted sub-surface tissue from a living being, such as a human. More particularly, the invention concerns a method for selectively destroying relatively deep sub-epidermal formations of unwanted tissue by heating water in the formations with a laser. This causes protein denaturing such as spatial protein conformation, without excessively damaging the unwanted tissue.

2. Description of the Related Art

In the field of cosmetic surgery, one important concern is the treatment of highly vascularized tissues, such as capillary blood vessels, strawberry hemangiomas, spider veins, telangiectasia, and the like. In this respect, many known techniques are aimed at eliminating or reducing such tissue. Some of these techniques, for example, include surgical dissection, sclerotherapy, and electro-cuttering. With surgical dissection, the patient is first anesthetized and then a cutting device such as a scalpel is used to surgically remove the vascularized tissue. With sclerotherapy, an alcohol-based substance is injected into veins for clotting of the veins. With electro-cuttering, a high-voltage scalpel is used to effectively "cut out" the unwanted tissue while coagulating blood in the region. Usually, healing of the treated tissue occurs after formation of a lesion on the skin's surface at the treatment site.

Although these techniques may be satisfactory in some applications, they may prove inadequate in certain other circumstances. For instance, certain patients may object to the pain caused by these procedures. Additionally, some patients may experience excessive bleeding, internally and/or externally. Furthermore, these procedures may inflame the treated tissue in some cases, and lead to healing by second tension. Another potential drawback of known methods concerns the post-treatment healing time, which some may find excessive. Further, in certain cases these techniques have been known to leave scars or other noticeable marks. Although sclerotherapy may be effective for treating big veins, some may complain that sclerotherapy is not sufficiently effective for smaller vessels such as capillary blood vessels.

In contrast to the techniques described above, some physicians have employed lasers to remove vascularized tissue. In particular, Dye lasers have been used to remove such tissue by destroying blood vessels. In particular, the Dye laser process works by exploding red blood cells and consequently erupting blood vessels. The Dye laser produces wavelengths that have little water absorption and therefore generates relatively deep tissue penetration. On the other hand, the Dye laser produces wavelengths that have a substantial level of oxyhemoglobin absorption. As a result, the Dye laser causes hemoglobin in the erythrocytes to be exploded, causing blood vessel eruption. For some patients, this process may not be satisfactory. In particular, with small formations such as spider veins and telangiectasia, this approach typically provides only a short term cosmetic correction of the tissue. Moreover, even after extended periods of convalescence, many of these patients still experience significant scarring.

In contrast to the Dye laser approach, some physicians have used infrared lasers at 1.9 $\mu$m and greater, such as Tm:YAG, Ho:YAG, Er:YSGG, Er:YAG, CO, and $CO_2$. These techniques often do not enjoy optimum results because of certain operating characteristics of the lasers. Chiefly, the laser is absorbed too readily by water in the patient's tissue, resulting in very poor penetration (e.g., 40–60 $\mu$m) of the laser into the patient's tissue. As a result, significant damage occurs to skin surface overlying the tissue region of interest. A need therefore exists for a more effective, less destructive, long term method of destroying unwanted vascular tissue.

SUMMARY OF THE INVENTION

Broadly, the present invention concerns a process for destroying relatively deep sub-epidermal formations of unwanted tissue by heating water in the formations with a laser to achieve spatial tissue conformation while avoiding excessive damage to the unwanted tissue. In an exemplary embodiment, a laser beam is produced to irradiate a target region of highly vascularized dermal tissue in a human or other living being with a blood circulatory system. The laser light preferably has a wavelength of about 1.45 $\mu$m–1.68 $\mu$m. This operating parameter provides the laser beam with a water absorption coefficient that is low enough to penetrate sufficiently into the target area; still, the water absorption and laser energy are high enough to achieve spatial conformation of vascularized tissue in the target area. To completely eliminate the unwanted tissue, the laser beam is systematically traced over the entire region. In accordance with the invention, the destroyed tissue may be eliminated by forceps, vaporized by the laser, or rejected as a necrotic tissue by the wound healing process.

The invention affords its users with a number of distinct advantages. Chiefly, the invention effectively destroys sub-surface regions of vascular tissue, without appreciable damage to the attached or surrounding tissue. As a result, patients experience little or no bleeding, inflammation, and pain during and after surgery. The invention also reduces post-operative healing time and scarring.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS

Figure 1:
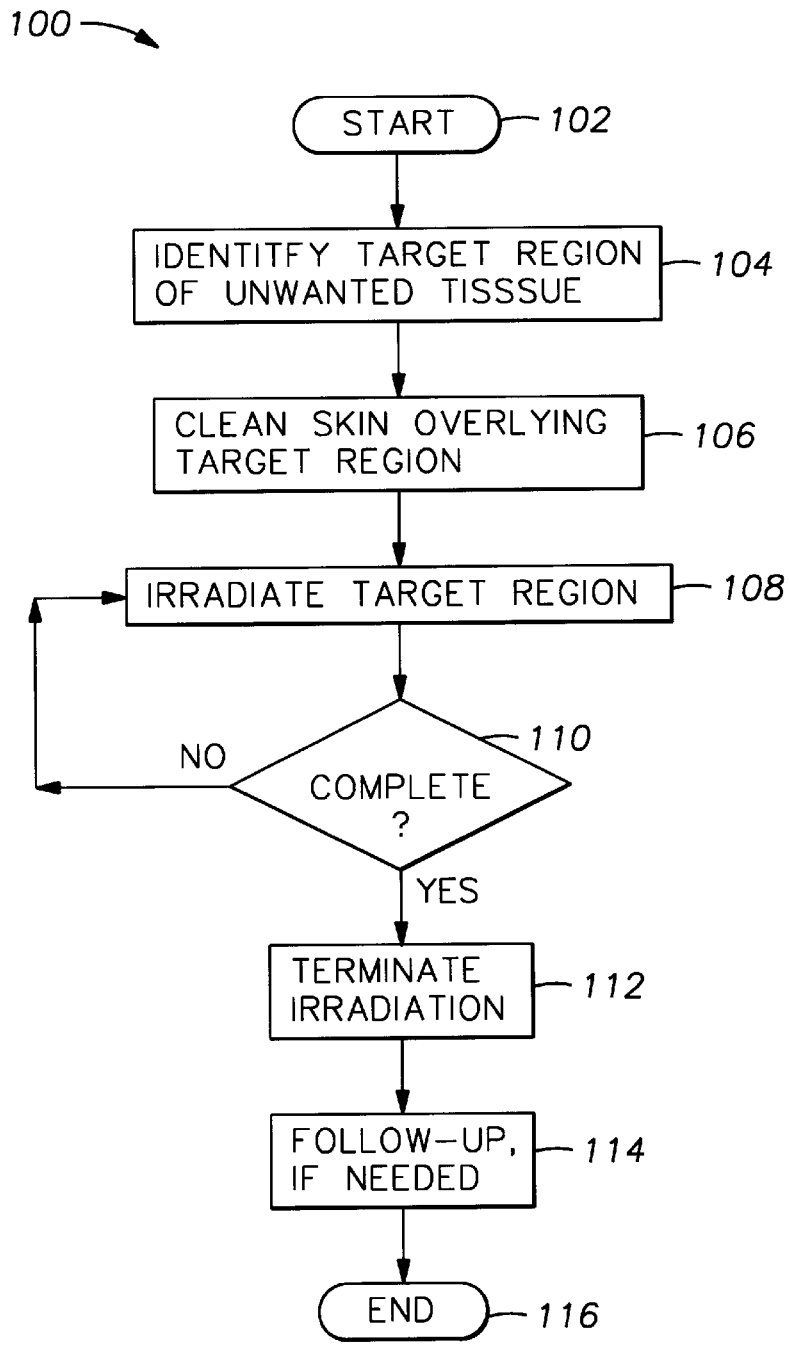
FIG. 1 is a flowchart showing a sequence of process steps in accordance with the invention.
Figure 2:
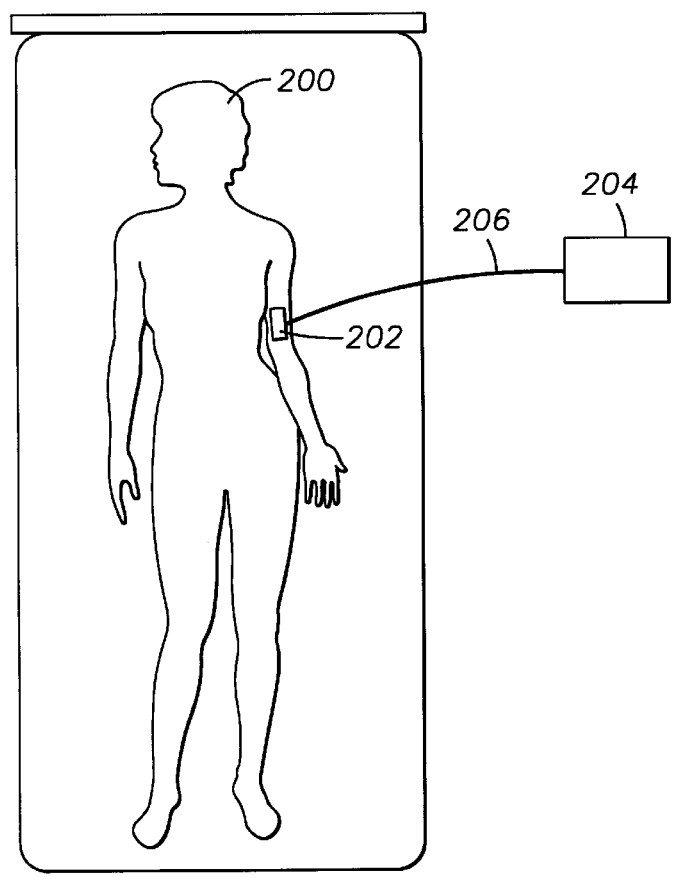
FIG. 2 is a diagram depicting the irradiation of a target region of tissue.

Broadly, the present invention concerns a process for destroying relatively deep formations of highly vascularized sub-surface tissue in a living being, such as a human or other organism with a blood circulatory system. The invention operates by heating water in dermal tissue formations with a laser to achieve spatial tissue protein conformation therein, while avoiding excessive damage to the region and the surrounding tissue. This is accomplished by using a laser with operating characteristics that are selected to achieve appropriate levels of water absorption, melanin absorption, and tissue penetration, to denature proteins in the unwanted tissue without excessively damaging that tissue or the surrounding, tissue.

LASER CHARACTERISTICS

Objectionable vascular tissue is typically located beneath the epidermis, about 0.5–2 mm beneath the skin's surface. Vascular tissue buried more deeply is not usually visible through the epidermis. The blood vessels of the vascular tissue typically include about 55% blood serum, 44% red blood cells (70% of which comprises water), and 1% white blood cells.

With these characteristics in mind, a number of different wavelengths of laser light were considered to identify a wavelength that provides a suitably low water absorption and complementarily effective penetration. The results appear below in Table 1.

TABLE 1

| ENTRY NO. | LASER | WAVE-LENGTH ($\mu$m) | AVERAGE WATER ABSORPTION (cm$^{-1}$) | AVERAGE MELANIN ABSORPTION (cm$^{-1}$) |
|---|---|---|---|---|
| 1 | Tm:YAG | 2.01 | ~100 | <1 |
| 2 | Ho:YAG | 2.10 | ~80 | <1 |
| 3 | Er:YSGG | 2.78 | ~700 | <1 |
| 4 | Er:YAG | 2.94 | ~1000 | <1 |
| 5 | CO | 5–6 | 300–3000 | <1 |
| 6 | CO$_2$ | 10.6 | ~1500 | <1 |
| 7 | Er:Glass | 1.54 | 1 | <1 |
| 8 | Dye | 0.55–0.65 | <10$^{-2}$ | 15–10 |

For the purpose of irradiating a target region located beneath the epidermis, the Er:Glass laser (entry no. 7) provides the best results. Specifically the Er:Glass laser has a low water and melanin absorption coefficient that facilitates penetration to the desired depth. In contrast, entry nos. 1–6 (i.e., those with wavelengths greater than or equal to about 2 $\mu$m) have absorption that is dominated by water in the tissue. This results in extremely shallow depth penetration, failing to extend past the epidermis. The Dye laser (entry no. 8) and other lasers with wavelengths less than or about 1 $\mu$m have a relatively lower overall absorption, which is dominated by skin melanin (tissue pigment). This lower water absorption coefficient results in deeper penetration with very little water absorption, but a significant amount of absorption in tissue melanin. The Er:Glass laser, operating at 1.54 $\mu$, combines the best features of both wavelength regimes, i.e. deeper penetration due to moderate absorption in both water and tissue melanin.

Another benefit of the Er:Glass laser is its compatibility with fiber optics, the usefulness of which is explained below. In particular, the Er:Glass laser produces an appropriate level of power to permit transmission through known fiber optic media.

In the preferred embodiment of the invention, a free-running Er:Glass laser is employed having operating parameters appropriate to the type of unwanted tissue being treated, as shown in Table 2 (below). In all cases, the laser is operated with sufficient power to achieve complete spatial protein conformation of tissue irradiated by the laser in the laser's range of penetration.

TABLE 2

| PATHOLOGY | PULSE ENERGY (J) | PULSE-WIDTH (ms) | PULSE REPETITION RATE (Hz) | SPOT SIZE DIAMETER (nm) |
|---|---|---|---|---|
| SPIDER VEIN | 0.8–1.6 | 2 | 0.5 | 0.6 |
| STRAWBERRY HEMANGIOMA | 3–4 | 2 | 1 | 0.6 |
| TELAN-GIECTASIA | 0.25 | 2 | 1 | 0.6 |
| KERATOSIS | 2.3–4.3 | 2 | 1 | 0.6 |
| CONDYLOMA | 4.5–4.7 | 2 | 1 | 0.6 |
| SKIN FIBROMA | 3.6–4.0 | 2 | 1 | 0.6 |
| BASELIOMA | 4.0–4.2 | 2 | 1 | 0.6 |
| PIGMENTED NEVUS | 3.5–3.8 | 2 | 1 | 0.6 |
| RHINOPHYMA | 1.8–2.5 | 2 | 1 | 0.6 |
| LEUKOPLAKIA | 2.5–3.0 | 2 | 1 | 0.6 |
| SQUAMOUS ADENO-CARCINOMA | 4.2–4.7 | 2 | 1 | 0.6 |
| INTRAMUCAL MYOMA | 4.54.7 | 2 | 1 | 0.6 |
| RECALCITRANT VERRUCAE | 3.1–3.5 | 2 | 1 | 0.6 |
| CORN | 4.0–4.2 | 2 | 1 | 0.6 |
| CALLUS | 2.7–3.5 | 2 | 1 | 0.6 |

OPERATIVE STEPS

FIG. 1 provides an example of the present invention in the form of process steps, 100, which are further explained with reference to FIGS. 2–5. The steps 100 are performed upon a patient 200 (FIG. 2) by an operator (not shown), such as a physician, nurse, or physician's assistant. After the process begins in task 102, the operator in task 104 identifies the boundaries of a "target region" 202 of unwanted tissue.

Figure 3:
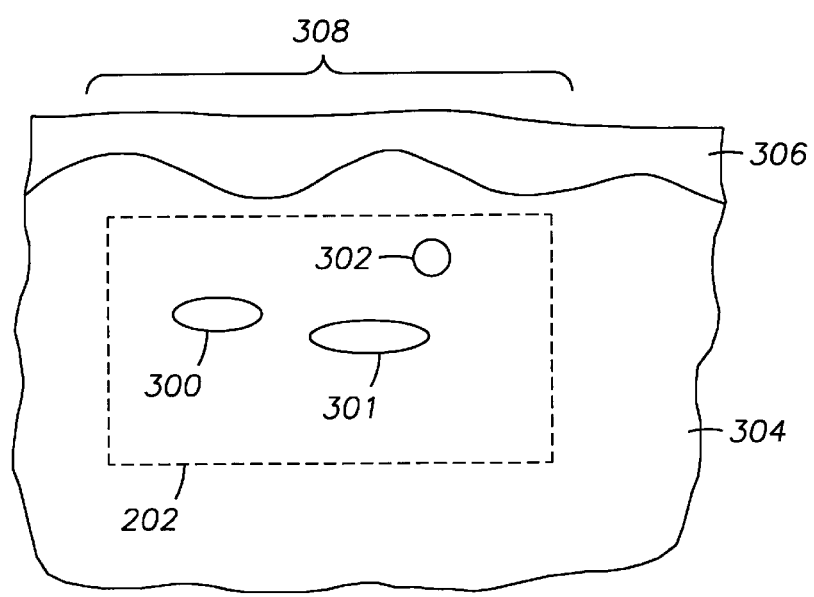
FIG. 3 is a cross-sectional view of the target region of tissue.

The target region 202 comprises a region of highly vascularized sub-surface tissue, such as an area of capillary blood vessels, strawberry hemangiomas, spider veins, telangiectasia, or another similar vascular formation. In the illustrated example, the target region 202 comprises a sub-epidermal region of capillary blood vessels 300–302, shown most clearly in FIG. 3. FIG. 3 depicts a cross-section of the capillary blood vessels 300–302 in relation to the dermis 304 and epidermis 306.

After identifying the target region in task 104, the operator in task 106 cleans the area of skin 308 overlying the target region. Then, in task 108, the operator irradiates the target region 202 with a laser beam (not shown) generated by a laser light source 204. Preferably, the laser beam comprises a beam of laser light generated by an Er:Glass laser with operating parameters established as shown above.

Figure 4:
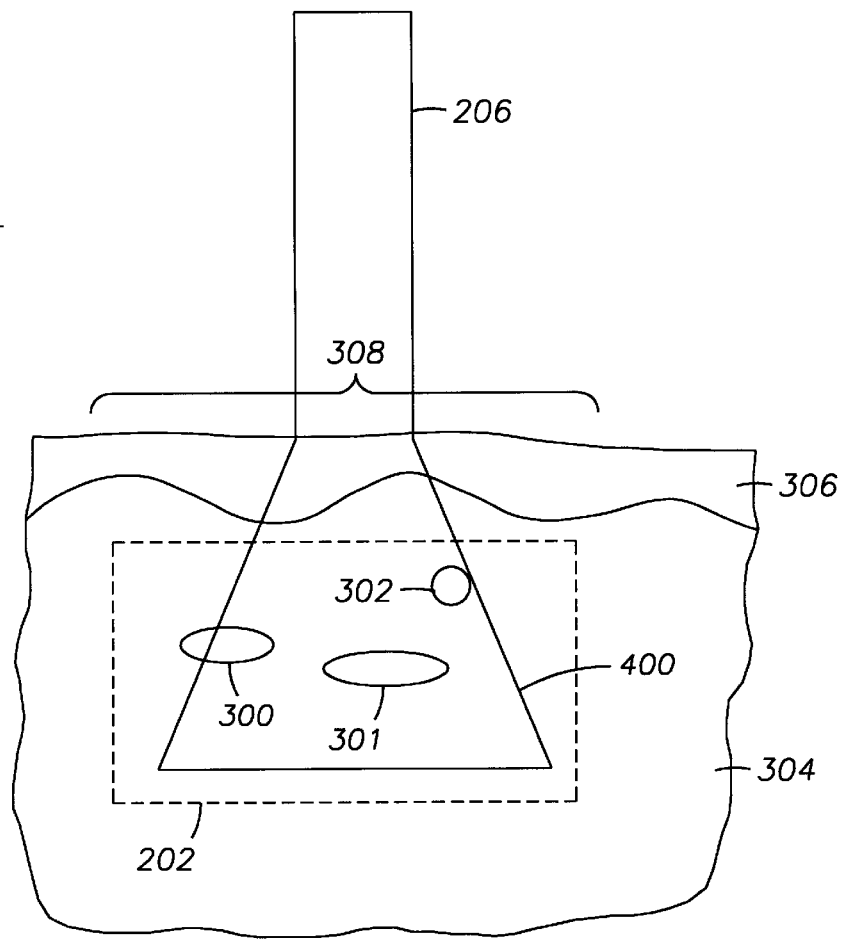
FIG. 4 is a cross-sectional view of the target region of tissue being irradiated by a laser beam.

In one embodiment (FIGS. 2, 4), the laser beam may be carried to the target region 202 by a fiber optic waveguide 206, coupled to the laser source 204. The waveguide 206 may comprise a flexible quartz member, for example, or another waveguide of suitable flexibility, optical clarity, etc. In this embodiment, the operator contracts a tip (not shown) of the fiber optic waveguide 206 with the target region 202. Alternatively (not shown), the laser beam may be directly impinged upon the target region 202. As shown in FIG. 4, when the laser beam enters the skin, it is diffused, thereby creating a broadened beam 400.

Figure 5:
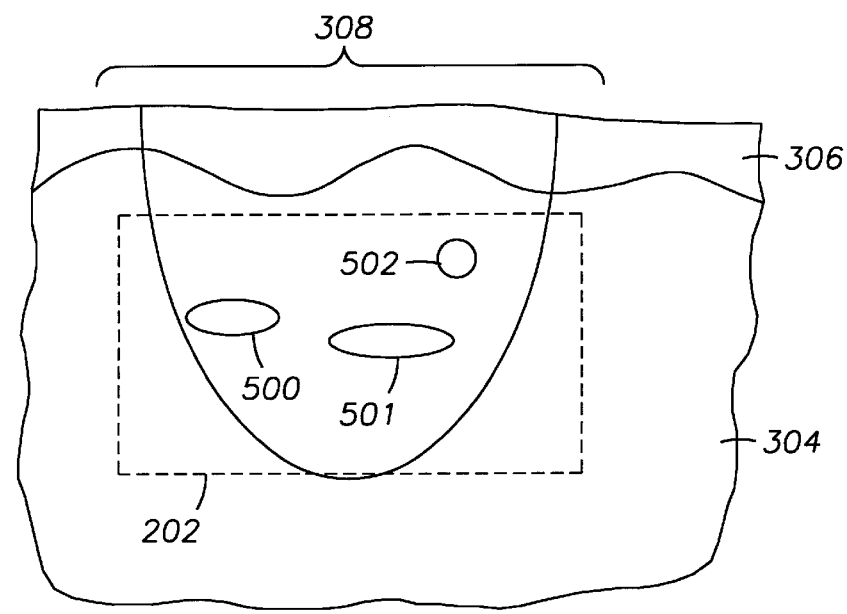
FIG. 5 is a cross-sectional view of the target region of tissue after irradiation by the laser beam.

When the laser beam contacts the skin 308 as shown in FIG. 4, the beam penetrates the skin 308 and passes into the target region 202. This level of penetration is possible due to the laser's moderate water absorption coefficient, which enables a desirable level of tissue penetration but prevents an excessive level of tissue penetration. In this respect, the laser's water absorption is sufficiently high to heat water present in the blood capillaries of the target region. This effectively denatures protein molecules in the target region, causing a spatial conformation of the unwanted tissue. In other words, the laser light is absorbed by the target region 202 causing a molecular transformation in the form of a local tissue necrosis within a zone of tissue coagulation. The laser beam therefore creates denatured regions 500–502 (FIG. 5).

During task 108, the operator must permit the laser beam to contact each portion of the target region 202 for a sufficient length of time. Namely, irradiation must be continued for enough time to heat the water in the vascular tissue sufficiently to result in spatial transformation of the tissue. Unlike prior techniques, however, if irradiation in one area is continued past the time of spatial conformation, the present invention does not cause burning, singeing, or other overheating. This is because the unwanted tissue, having undergone spatial conformation, is no longer receptive to further transformation by the laser. As a result, the irradiation of task 108 provides a safe yet effective technique for treating the target region 202.

After the target region 202 is irradiated as discussed above in task 108, the operator visually inspects the target region in query 110 to determine whether the irradiation is complete. If the initial traversal of the target region 202 has inadvertently missed some areas, or failed to sufficiently denature some areas, the operator returns to task 108 for additional treatment of the missed areas with the laser beam. After process is complete, however, the operator stops irradiating the target region in task 112.

After task 112, follow-up treatment may be performed in task 114, if needed. In particular, denatured tissue of the target region 202 may be removed and then further irradiation of the target region 202 may be performed. In one embodiment, the denatured region may be removed with a scalpel and forceps soon after the initial laser treatment of task 108. This enables the operator to treat deeper, underlying areas of the target region 202 beneath those areas initially treated. In an alternative embodiment, the operator may wait until the treated target region 202 heals sufficiently to form a hardened layer of dried blood, i.e., a scab. Then, the operator may remove the scab with a forceps and irradiate the target region again.

OTHER EMBODIMENTS

While there have been shown what are presently considered to be preferred embodiments of the invention, it will be apparent to those skilled in the art that various changes and modifications can be made herein without departing from the scope of the invention as defined by the appended claims.

For example, many other lasers may be used instead of an Er:Glass laser. For instance, other lasers may be frequency-modified to achieve a wavelength within a range of 1.45 $\mu$m to 1.68 $\mu$m. Particularly, this can be accomplished using frequency doubling, frequency tripling, of Raman shifting, or by employing a different rod, a diode laser, or a diode-pumped solid state or Dye laser. Additionally, a Q-switched laser may be used, instead of a free-running system.

What is claimed is:

1. A method of treating discolored regions of vascularized dermal tissue, comprising the steps of:

generating a laser beam having an absorption coefficient of about 1 $cm^{-1}$ in water;

directing the laser beam toward a target region of dermal tissue;

irradiating the target region with the laser beam for heating of the water in the target region to achieve spatial tissue conformation therein; and discontinuing irradiation of the target region.

2. A method of treating a vascularized tissue region of sub-surface dermal flesh, comprising the steps of irradiating a target area of the dermal tissue region with a laser beam having operating parameters such that the laser beam has an absorption coefficient of about 1 $cm^{-1}$ in water, said laser beam penetrating through the surface and up to about 2 mm beneath the surface into the target area and heating water in the target region to spatially conform and cause necrosis to vascularized tissue therein.

3. The method of claim 2, further comprising the steps of tracing the laser beam along a selected path to irradiate a selected portion of the tissue region.

4. The method of claim 3, wherein the selected portion comprises all of the tissue region.

5. The method of claim 3, wherein the selected path comprises a continuous path.

6. A method of treating unwanted tissue from a blood-circulating living being, comprising the steps of:

aiming a laser beam at a target region of vascularized dermal tissue, the beam having a wavelength of about 1.45 $\mu$m to 1.68 $\mu$m;

continuing to aim the laser beam at the target region a sufficient time to heat water in the target region adequately to achieve protein denaturing of the target region; and terminating interaction between the laser beam and the target region.

7. The method of claim 6, further comprising generating the laser beam wherein the laser beam has a wavelength of about 1.54 $\mu$m.

8. A method for treating unwanted sub-surface dermal tissue of a living being having a blood circulatory system, comprising the steps of:

aiming a laser beam through the surface at a target region of the sub-surface dermal tissue, the beam having a wavelength of about 1.45 $\mu$m–1.68 $\mu$m;

continuing to aim the laser beam at the tissue a sufficient time to heat water in the sub-surface target region to achieve protein denaturing and tissue necrosis of vascularized tissue in the target region; and discontinuing aiming of the laser beam at the target region of tissue.

9. A method of treating dermal tissue beneath a skin surface in a living being, comprising the steps of:

directing a laser beam through the skin surface to irradiate a target region of the dermal tissue, the laser beam having a wavelength of about 1.45 $\mu$m to 1.68 $\mu$m;

continuing irradiation of the target region for sufficient heating of water in the target region to denature tissue proteins of the target region and cause tissue necrosis in the target region; and ending irradiation of the target region by the laser beam.

10. The method of claim 1, wherein the living being comprises a human being.

11. The method of claim 1, further comprising using an Er:Glass laser to generate the laser beam.

12. The method of claim 1, further comprising frequency-doubling output of an Er:YAG laser to generate the laser beam.

13. The method of claim 1, wherein the directing of the laser beam comprises directing the laser beam to a strawberry hemangioma.

14. The method of claim 1, wherein the directing of the laser beam comprises directing the laser beam to a spider vein.

15. The method of claim 1, wherein the directing of the laser beam comprises directing the laser beam to a telangiectasia.

16. The method of claim 1, wherein the directing of the laser beam comprises directing the laser beam to a tumor of vascularized mucous.

17. The method of claim 1, wherein the irradiating step is performed by coupling a laser light source to the target region with an optical waveguide.

18. The method of claim 1, wherein the directing of the laser beam comprises directing the laser beam to a target region located a depth of less than about 2 millimeters beneath the skin surface of the living being.

19. The method of claim 1, further comprising generating the laser beam wherein the laser beam has a pulse energy of about 0.25 to 4 Joules.

20. The method of claim 1, further comprising generating the laser beam wherein the laser beam has a pulsewidth of about 2 milliseconds.

21. The method of claim 1, further comprising generating the laser beam wherein the laser beam has a pulse repetition rate of about 0.5 to 1 Hertz.

22. The method of claim 1, further comprising generating the laser beam wherein the laser beam has a spot size diameter of about 0.6 millimeters.

23. The method of claim 1, further comprising generating the laser beam by Q-switching a laser.

24. The method of claim 1, further comprising generating the laser beam using a free running laser.

25. The method of claim 1, further comprising the steps of:

removing at least a part of the denatured tissue to reveal underlying areas not completely denatured;

irradiating the underlying areas with a laser beam having a wavelength of about 1.45 $\mu$m to 1.68 $\mu$m;

continuing irradiation of the underlying area for sufficient heating of water in the underlying area to denature tissue proteins therein; and ending irradiation of the underlying areas by the laser beam.

26. The method of claim 25, wherein the removing step comprises the steps of removing a scab formed by healing of the denatured tissue over a period of time.

27. The method of claim 25, wherein the removing step comprises the step of surgically extracting at least a part of the denatured tissue prior to formation of a scab thereover.

* * * * *